(12) United States Patent
McLaren

(10) Patent No.: US 8,702,720 B2
(45) Date of Patent: Apr. 22, 2014

(54) TASSEL TIP WIRE GUIDE

(75) Inventor: Douglas E. McLaren, Rancho Murieta, CA (US)

(73) Assignee: Cook Medical Technologies LLC, Bloomington, IN (US)

( * ) Notice: Subject to any disclaimer, the term of this patent is extended or adjusted under 35 U.S.C. 154(b) by 1155 days.

(21) Appl. No.: 11/743,745

(22) Filed: May 3, 2007

(65) Prior Publication Data

US 2007/0260158 A1 Nov. 8, 2007

Related U.S. Application Data

(60) Provisional application No. 60/797,100, filed on May 3, 2006.

(51) Int. Cl.
*A61F 11/00* (2006.01)
(52) U.S. Cl.
USPC ...................... 606/108; 604/164.01
(58) Field of Classification Search
USPC .......................................... 27/24.1
See application file for complete search history.

(56) References Cited

U.S. PATENT DOCUMENTS

| | | |
|---|---|---|
| 3,521,620 A | 7/1970 | Cook |
| 3,550,591 A | 12/1970 | MacGregor |
| 4,166,469 A | 9/1979 | Littleford |
| 4,167,939 A | 9/1979 | Storz |
| 4,243,050 A | 1/1981 | Littleford |
| 4,306,562 A | 12/1981 | Osborne |
| 4,345,606 A | 8/1982 | Littleford |
| 4,411,654 A | 10/1983 | Boarini et al. |
| 4,412,832 A | 11/1983 | Kling et al. |
| RE31,855 E | 3/1985 | Osborne |
| 4,548,206 A | 10/1985 | Osborne |
| 4,577,637 A | 3/1986 | Mueller, Jr. |
| 4,592,341 A | 6/1986 | Omagari et al. |
| 4,596,559 A | 6/1986 | Fleischhacker |
| 4,631,054 A | 12/1986 | Kim |
| 4,747,833 A | 5/1988 | Kousai et al. |
| 4,773,394 A | 9/1988 | Reichstein et al. |
| 4,776,846 A | 10/1988 | Wells |
| 4,781,690 A | 11/1988 | Ishida et al. |
| 4,799,474 A | 1/1989 | Ueda |
| 4,801,294 A | 1/1989 | Okada |
| 4,813,929 A | 3/1989 | Semrad |
| 4,883,468 A | 11/1989 | Kousai et al. |
| 4,934,340 A | 6/1990 | Ebling et al. |
| 4,983,168 A | 1/1991 | Moorehead |
| 4,997,424 A | 3/1991 | Little |
| 5,024,617 A | 6/1991 | Karpiel |
| 5,052,998 A | 10/1991 | Zimmon |
| 5,055,101 A | 10/1991 | McCoy |
| 5,078,701 A | 1/1992 | Grassi et al. |
| 5,109,830 A | 5/1992 | Cho |
| 5,129,890 A | 7/1992 | Bates et al. |
| 5,159,861 A | 11/1992 | Anderson |
| 5,195,978 A | 3/1993 | Schiffer |

(Continued)

*Primary Examiner* — Victor Nguyen
*Assistant Examiner* — Kevin Everage
(74) *Attorney, Agent, or Firm* — Brinks Gilson & Lione

(57) ABSTRACT

An improved wire guide and method for cannulating a bodily lumen, such the biliary tree are provided for procedures such as endoscopic retrograde cholangiopancreatography (ECRP). The wire guide and cannulation method minimizes the potential for trauma to the ducts while reducing the chances of disconnecting the wire guide from newer access devices. Generally, the wire guide includes an atraumatic tassel tip which is operable between delivery and deployed configurations.

16 Claims, 3 Drawing Sheets

(56) References Cited

U.S. PATENT DOCUMENTS

| | | |
|---|---|---|
| 5,213,111 A | 5/1993 | Cook et al. |
| 5,234,003 A | 8/1993 | Hall |
| 5,243,996 A | 9/1993 | Hall |
| 5,251,640 A | 10/1993 | Osborne |
| 5,320,602 A | 6/1994 | Karpiel |
| 5,325,746 A | 7/1994 | Anderson |
| 5,354,257 A | 10/1994 | Roubin et al. |
| 5,383,849 A | 1/1995 | Johlin, Jr. |
| 5,520,697 A * | 5/1996 | Lindenberg et al. ......... 606/108 |
| 5,776,079 A | 7/1998 | Cope et al. |
| 5,885,258 A * | 3/1999 | Sachdeva et al. ............ 604/530 |
| 6,254,550 B1 | 7/2001 | McNamara et al. |
| 6,348,041 B1 | 2/2002 | Klint |
| 6,383,146 B1 | 5/2002 | Klint |
| 6,502,606 B2 | 1/2003 | Klint |
| 6,613,002 B1 | 9/2003 | Clark et al. |
| 6,712,827 B2 * | 3/2004 | Ellis et al. ..................... 606/108 |
| 7,001,345 B2 | 2/2006 | Connors, III et al. |
| 7,316,706 B2 * | 1/2008 | Bloom et al. ................. 606/232 |
| 2004/0193092 A1* | 9/2004 | Deal ................................ 604/8 |
| 2006/0155366 A1* | 7/2006 | LaDuca et al. .............. 623/1.23 |
| 2007/0051377 A1* | 3/2007 | Douk et al. ................... 128/897 |

* cited by examiner

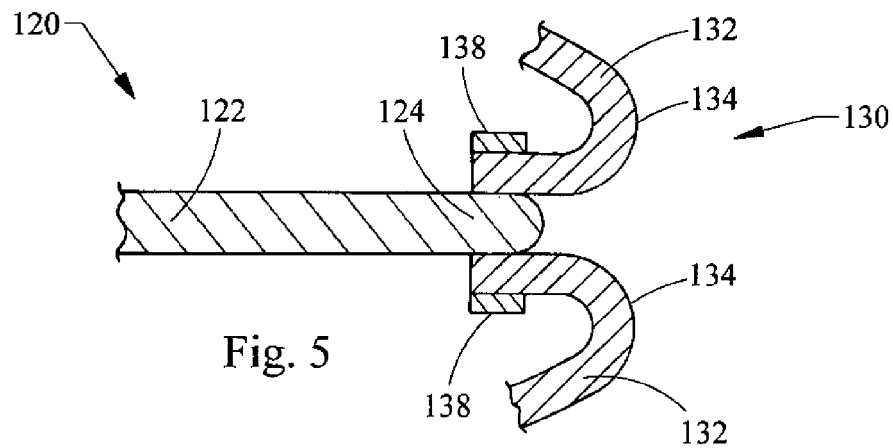
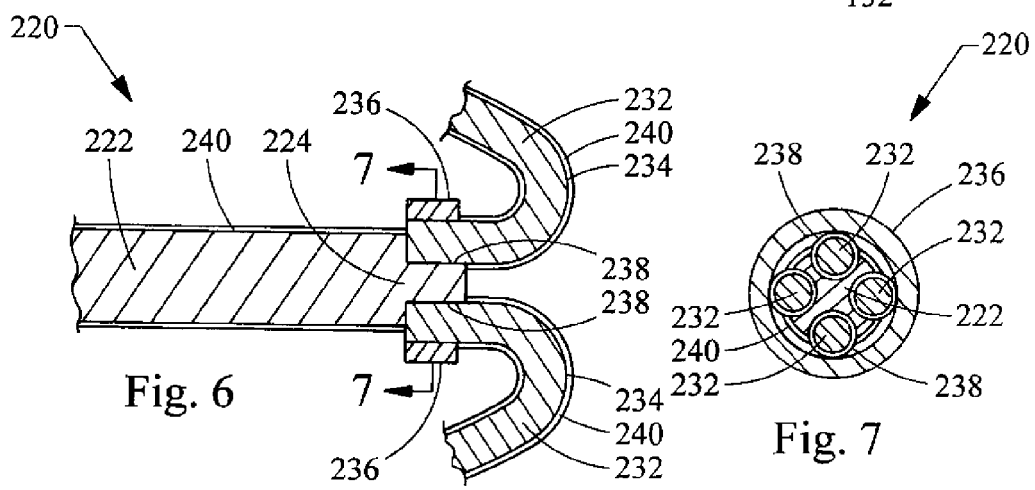
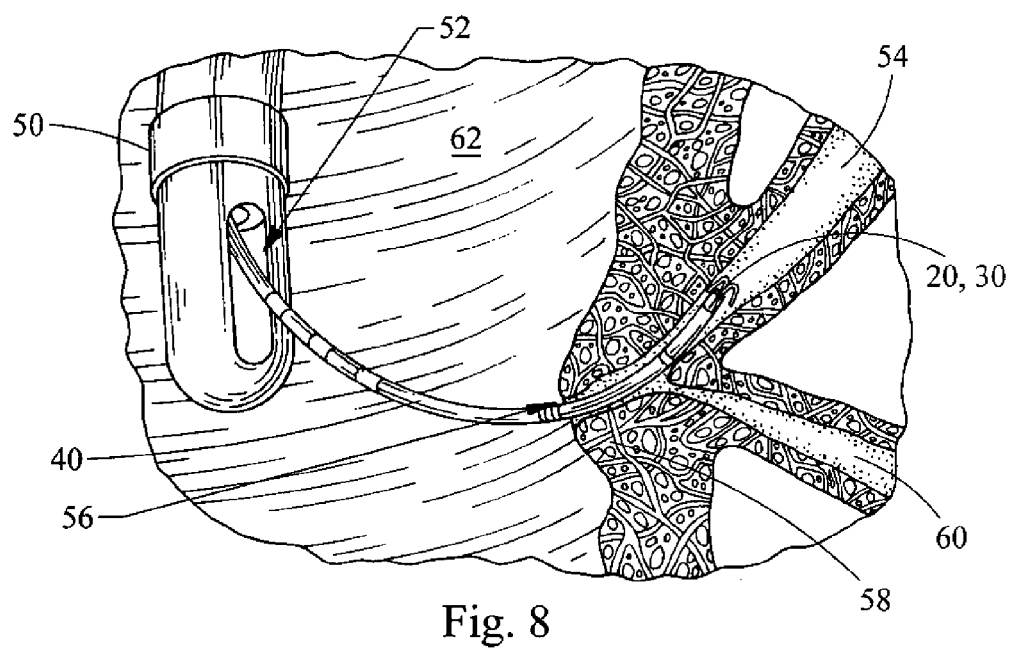

TASSEL TIP WIRE GUIDE

CROSS-REFERENCE TO RELATED APPLICATIONS

This application claims the benefit of U.S. Provisional Application Ser. No. 60/797,100, filed on May 3, 2006, entitled "TASSEL TIP WIRE GUIDE," the entire contents of which are incorporated herein by reference.

FIELD OF THE INVENTION

The present invention relates generally to wire guides for intracorporeal procedures, and more particularly relates to wire guides for assisting in cannulation during endoscopic procedures such as endoscopic retrograde cholangiopancreatography (ERCP).

BACKGROUND OF THE INVENTION

ERCP is a study of the ducts that drain the liver and pancreas. Generally, the liver produces bile that is concentrated by the gallbladder and delivered to the duodenum (upper small intestine) via the common bile duct. The pancreatic duct joins the bile duct at the papilla of Vater where they drain into the duodenum through the sphincter of Oddi. ERCP generally includes cannulation of the biliary tree (which includes the bile duct, pancreatic duct, and hepatic ducts of the liver) by delivering a catheter through the working channel of a duodenoscope and into the biliary tree. A contrast medium is injected through the catheter to provide for diagnosis of problems in the liver, gallbladder, biliary tree and pancreas, such as gallstones, inflammatory strictures, leaks or cancer. Exemplary ERCP catheters are described in U.S. Pat. Nos. 5,320,602 and 5,383,849.

A wire guide is often used to assist in navigation of the catheter (or other endoscopic access devices such as sphinctertomes, balloons, biopsy devices, stent delivery catheters, dilators, etc.) through the sphincter of Oddi and into the biliary tree, often referred to as cannulation. Wire guides may also be used for deep cannulation of the biliary tree. Wire guides, however, carry the risk of trauma to structured segments of the bile or pancreatic ducts which can result in life-threatening infection, perforation or pancreatitis. Additionally, with the advent of new access devices permitting rapid exchange of multiple devices without the need for traditional "over the wire" or "long wire" exchanges (see, e.g., U.S. Pat. Pub. No. 2005/0059890, the disclosure of which is hereby incorporated by reference in its entirety) there exists the possibility for unintentional disconnection of the access device and wire guide.

Accordingly, there exists a need for a wire guide that assists in cannulation of the biliary or pancreatic ducts and minimizes the potential for trauma to the ducts. At the same time, it would also be desirable to reduce the chances of disconnection of the wire guide from newer access devices providing rapid exchange.

BRIEF SUMMARY OF THE INVENTION

The present invention provides an improved wire guide and method for cannulating a bodily lumen such the biliary tree. The wire guide and cannulation method minimizes the potential for trauma to the ducts while reducing the chances of disconnecting the wire guide from newer access devices.

According to one embodiment constructed in accordance with the teachings of the present invention, the wire guide includes the main body having a distal end, and a tassel tip formed at the distal end. The tassel tip is defined by a plurality of strands having free end portions. The tassel tip is operable between a delivery configuration and a deployed configuration. The free end portions of the plurality of strands are positioned adjacent the longitudinal axis in the delivery configuration, and are spaced radially from the longitudinal axis in the deployed configuration. The strands curve away from the longitudinal axis to define atraumatic peaks in the deployed configuration.

According to more detailed aspects, each strand further includes a connecting portion and a middle portion between the connecting portion and the free end portion. The middle portion is curved in the deployed configuration to define atraumatic peaks for safe navigation of the wire guide. The free end portions are positioned distally relative to the middle portions in the delivery configuration, and the free end portions are positioned proximally relative to the middle portions in the deployed configuration. The free ends of the plurality of strands are radially spaced apart a distance greater than a diameter of the main body, and thus form an umbrella shape at the distal end. The plurality of strands preferably extend proximally along side the outside of the main body. The plurality of strands are formed of a flexible material having sufficient strength to form the umbrella shape in the deployed configuration.

According to still further aspects, the distal end of the main body may be constructed of a plurality of wires or may be constructed of a solid or tubular wire. When the distal end of the main body is constructed of a plurality of wires, the distal portions of the plurality of wires may be used to form the plurality of strands of the tassel tip. A hub at the distal end of the main body is used to band together the plurality of wires. When the distal end of the main body is constructed as a solid wire, the distal portion preferably includes a plurality of channels receiving a portion of the plurality of strands to reduce the overall package size, or alternatively the strands may be unitarily and integrally formed from the solid wire.

According to another embodiment in accordance with the teachings of the present invention, a method for performing cannulation of a bodily lumen is provided. The method generally includes the steps of coupling the above-described wire guide to an access device, whereby the plurality of strands are contained within a passageway of the access device. The wire guide is translated distally relative to the access device, the distal movement of the tassel tip causes it to take a deployed configuration wherein the middle portion of each of the strands curves to define atraumatic peaks for safe navigation of the wire guide within the bodily lumen. Preferably, the bodily lumen is the biliary tree of a mammalian patient, and the method further includes a step of placing a duodenoscope into the duodenum of the patient. Here, the advancing step includes passing the wire guide and access device as a unit through a channel of the duodenoscope and through a sphincter of Oddi leading to the biliary tree.

BRIEF DESCRIPTION OF THE DRAWINGS

The accompanying drawings incorporated in and forming a part of the specification illustrate several aspects of the present invention, and together with the description serve to explain the principles of the invention. In the drawings:

FIG. 5 depicts a cross-sectional view of an alternate embodiment of the wire guide depicted in FIGS. 1-4;

FIG. 6 depicts a cross-sectional view of yet another alternate embodiment of the wire guide depicted in FIGS. 1-4;

FIG. 7 depicts a cross-sectional view, taken about the line 7-7 of FIG. 6;

FIG. 8 depicts a schematic view, partially in cross-section, of the wire guide of FIGS. 1-4 in the process of cannulating the biliary tree;

DETAILED DESCRIPTION OF THE INVENTION

Figure 1:
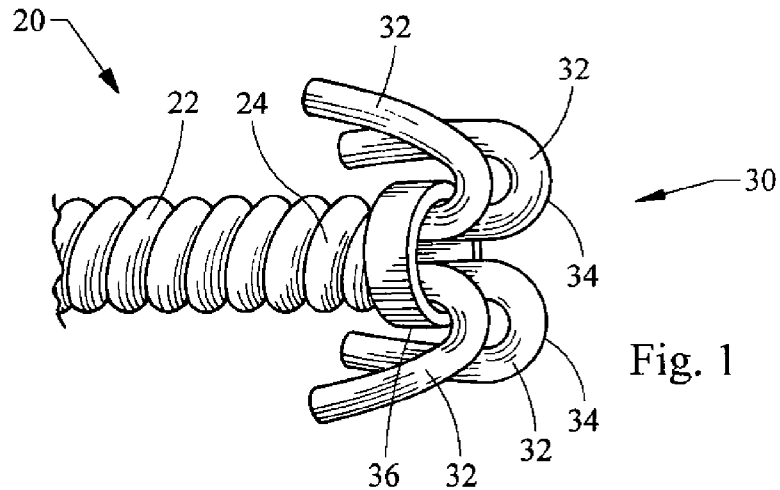
FIG. 1 depicts a perspective view of a wire guide constructed in accordance with the teaching of the present invention.

Turning now to the figures, FIG. 1 depicts a deployed configuration of a wire guide 20 constructed in accordance with the teachings of the present invention. The wire guide generally includes the main body 22 having a distal end 24 which includes a tassel tip 30. The tassel tip 30 is formed by a plurality of strands 32. Preferably the number of strands 32 is greater than or equal to 3, and the currently preferred configuration of four strands has been depicted in the figures. Each of the strands 32 is constructed of a flexible material that permits them to retroflex, i.e. curve away from a longitudinal axis of the wire guide 20 and extend proximally to form an umbrella or tassel shape as shown in FIG. 1. The length of tassels 32 and their flexibility are selected to provide the desired curvature having atraumatic peaks 34 to prevent damage to the bodily structures being navigated.

The strands 32 may be hydrophilic and/or radiopaque. For example, the strands 32 may be formed of a metal such as platinum, stainless steel, or an alloy such as a superelastic alloy of nickel titanium, and can further include a hydrophilic coating that can be formed of a hydrophilic polymer such as polytetrafluorethylene (PTFE), Teflon™, silicone, glycerin, modified polyurethanes or various blends. Of course, the strands 32 can be formed of suitable plastics such as polytetrafluorethylene (PTFE), polyethylene ether ketone (PEEK), polyvinylchloride (PVC), polyamide including Nylon®, polyimide, polyurethane, polyethylene (high, medium or low density), and elastomers such as Santoprene®, the plastic being selected (or combined with other materials) to provide the desired properties noted above. The construction of the strands 32 exhibits a suitable balance between flexibility and strength to form the depicted umbrella shape and define the atraumatic peaks 34. Preferably each strand 32 has a diameter less than or equal to the radius of the main body 22, depending on material selection.

Figures 2, 3:
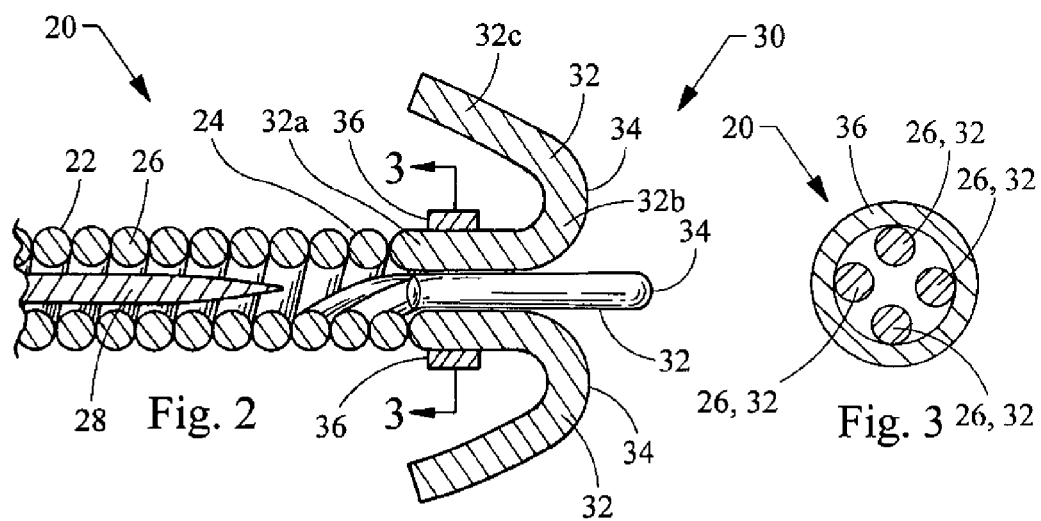
FIG. 2 depicts a cross-sectional view, taken from the side, of the wire guide depicted in FIG. 1.
FIG. 3 depicts a cross-sectional view, taken about the line 3-3 of FIG. 2.

As best seen in FIGS. 2 and 3, the main body 22 of the wire guide includes a plurality of wires 26 disposed over a mandrel 28. It will be recognized that the mandrel 28 may be dispensed with, and the wires 26 may be stranded together such as by twisting or braiding. Preferably, the number of wires 26 equals the number of strands 32 of the tassel tip 30 such that the wires 26 may be used to form the strands. As such, the distal end 24 of the main body 22 includes a hub 36 which is used to band the wires 26 together. Distally from the hub 36, the wires 26 form the strands 32 which are free to curve and extend proximally to define the atraumatic peaks 34. Specifically, each strand 32 includes a connecting portion 32a connected to the main body 22, a middle portion 32b curving to form the atraumatic peaks 32b, and a free end portion 32c opposite the connecting portion 32a.

Figure 4:
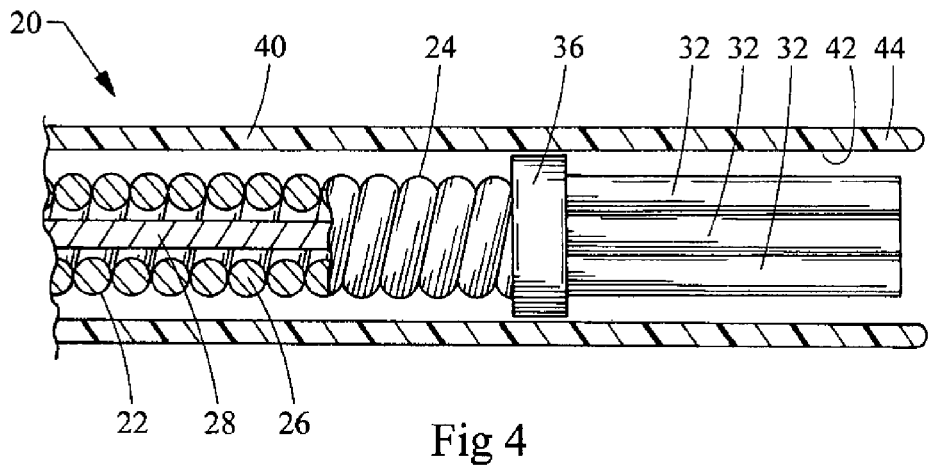
FIG. 4 depicts a side view, partially in cross-section, of a delivery configuration of the wire guide depicted in FIGS. 1-3.

As shown in FIG. 4, a delivery configuration of the wire guide 20 has been depicted. As discussed in the Background section, the wire guide 20 has particular application in cannulation of the biliary tree during procedures such as ECRP, and thus may be placed at the entrance of the biliary tree in conjunction with an access device. The access device has been depicted as a simple cannula or catheter 40 in FIG. 4. The catheter 40 includes an internal passageway 42 that is sized to receive the wire guide 20 and permit translation relative thereto. As such, the wire guide 20 may be translated beyond the open distal end 44 of the catheter 40 whereby the flexible nature of the strands 32 causes them to take their deployed configuration depicted in FIG. 1. From the deployed configuration, proximal translation of the wire guide 20 relative to the catheter 40 will cause the catheter's distal end 44 to impinge upon the inner curvature of the strands 32, which will again cause them to extend distally as the wire guide 20 is withdrawn into the passageway 42 of the catheter 40.

In the delivery configuration depicted in FIG. 4, the strands 32 extend distally to define a compact shape that is suitable for being received within the passageway 42 of the catheter 40. That is, the free end portions 32c of the strands 32 are positioned adjacent to the longitudinal axis of the wire guide 20 and main body 22 in the delivery configuration. In the deployed configuration of FIGS. 1 and 2, the free end portions 32c are spaced radially outwardly from the longitudinal axis of the wire guide 20 and main body 22. It can also be seen in the figures that the free end portions 32c are positioned distally relative to the middle portions 32b in the delivery configuration (FIG. 4), and then proximally relative to the middle portions 32b in the deployed configuration (FIG. 2). That is, the strands 32 retroflex to define the umbrella shape.

It will be recognized by those skilled in the art that the main body 22 of the wire guide may take many forms, including multiple wound wires or single wires which may be solid or tubular in form, as well as combinations thereof (see, e.g., U.S. Pat. No. 5,243,996). For example, FIG. 5 depicts a wire guide 120 having a main body 122 formed of a single solid wire. As with the previous embodiment, the distal end 124 of the main body 122 includes a tassel tip 130 formed by a plurality of strands 132 defining atraumatic peaks 134. The plurality of strands 132 may be attached to the distal end 124 by many fastening methods including soldering, welding, adhesives or mechanical deformation. As depicted, a hub 138 is used to band or crimp the plurality of strands 132 to the distal end 124 of the main body 122.

Similarly, FIGS. 6 and 7 depict another embodiment of the wire guide 220 which uses a solid wire main body 222. In this embodiment, the distal end 224 of the main body 222 includes a plurality of channels 238 sized to receive at least a portion of the plurality of strands 232. As with the previous embodiments, the strands 232 define an atraumatic peak 234 and are connected to the distal end 222 through use of a hub 236 that is used to band the strands 232 to the main body 222. It can be seen that the strands 232 have a generally circular cross-sectional shape, and thus the channels 238 are circular or semi-circular. Here, a hydrophilic coating 240 has been shown on both the main body 222 and each of the plurality of strands 232. As noted above, a hydrophilic coating may optionally be used with any embodiment of the present invention.

Figure 9:
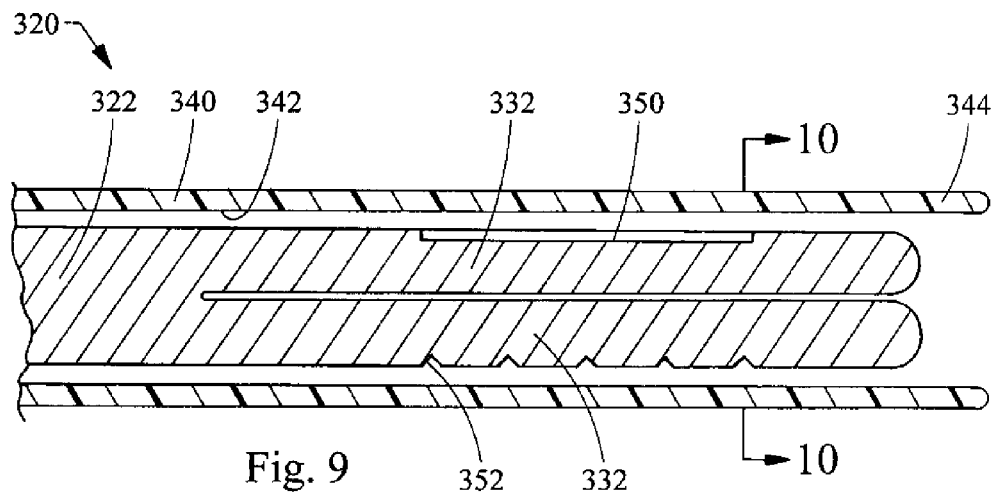
FIG. 9 depicts a cross-sectional view of still yet another alternate embodiment of the wire guide depicted in FIGS. 1-4.
Figure 10:
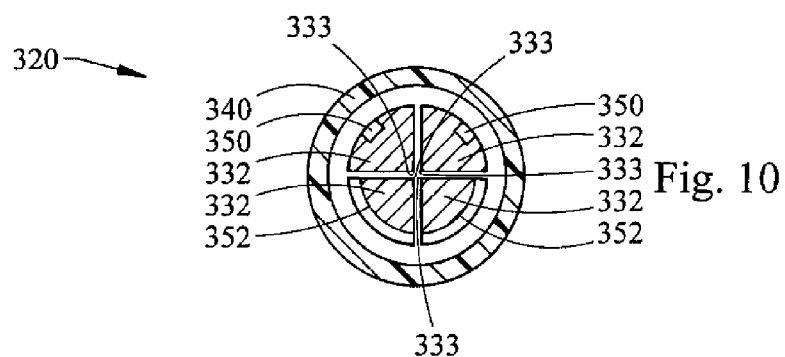
FIG. 10 is a cross-sectional view taken about the line 10-10 of FIG. 9.
Figure 11:
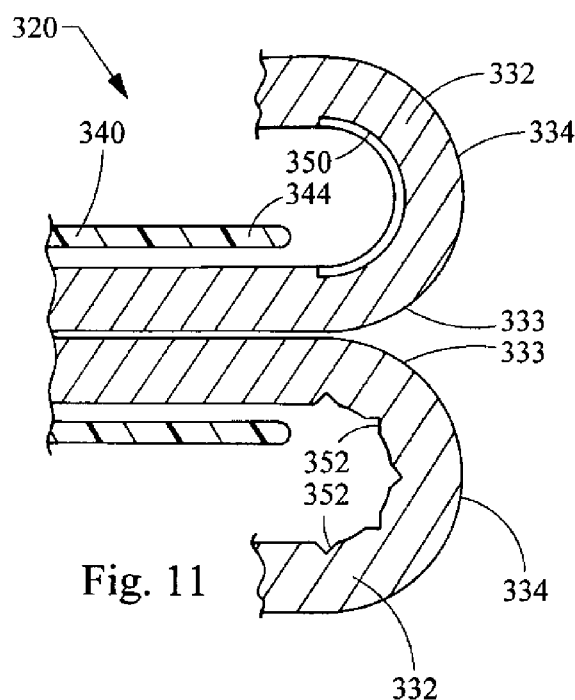
FIG. 11 is a cross-sectional view of the wire guide depicted in FIGS. 9-10 shown in a deployed configuration.
Figure 12:
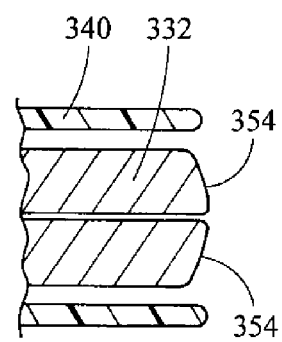
FIG. 12 is a cross-sectional view of an alternate tip configuration for the wire guide depicted in FIGS. 9-11.

Yet another embodiment of the wire guide 320 has been depicted in FIGS. 9-11. A solid wire main body 222 is cut, such as by laser or other material removal processes, to unitarily and integrally form the plurality of strands 332. As best seen in FIG. 10, any number of strands 332 may be formed, each having a pie-shaped cross-section. As with the prior embodiments, the strands 332 are structured to form a delivery configuration (FIG. 9) for positioning within the passageway 342 of a delivery catheter 340. It will also be seen in FIG. 12 that the distal ends 354 of each of the strands 332, rather than each having a semi-spherical tip as shown in FIG. 9, may together form a semi-spherical or bullet-shaped tip in the delivery configuration.

In the deployed configuration of FIG. 11, the free ends of strands 332 move away from the longitudinal axis and retroflex (i.e. curve and extend proximally) to define the atraumatic peaks 334 and general umbrella shape. It will be recognized that the strands 332 may include grooves 350 or notches 352 or other material deformations to improve the flexibility of the strands 332 and their operability into the deployed configuration of FIG. 11. Preferably, an inner edge 333 of each strand 332 is further formed to be curved, such as by a filet, to define the atraumatic peaks 334 of each of the strands 332.

The present invention includes a method for performing cannulation of a body lumen employing the wire guides as described above. With reference to FIGS. 1, 4 and 8, the method generally comprises the steps of coupling a wire guide 20 to an access device 40. In FIG. 4, the wire guide 20 is coupled to the catheter 40 by positioning the wire guide 20, or at least its distal tassel tip 30, within the internal passageway 42 of the catheter 40. The plurality of strands 32 extend distally and are contained within the passageway 42. The wire guide 20 and access device 40 are advanced as a unit into the bodily lumen, such as the common bile duct depicted in FIG. 8, although this step may not be used depending on the particular body structures being cannulized. The wire guide 20 may then be translated distally relative to the access device 40, whereby the distal movement of the tassel tip 30 causes it to take a deployed configuration such as depicted in FIGS. 1 and 8.

When the bodily lumen is the bile duct 54, pancreatic duct 60, or another portion of the biliary tree, the method may further include the steps of placing a duodenoscope 50 into the duodenum 62 of the mammalian patient. Preferably, the duodenoscope 50 is guided until its opening 52 is in close proximity to the papilla of Vater 56 and the sphincter of Oddi 58 which lead to the common bile duct and the pancreatic duct 60. As such, the advancing step includes passing the wire guide 20 and access device 40 as a unit through the working channel of the duodenoscope 50 and through the sphincter of Oddi 58. The wire guide 20 may then be advanced to provide deep cannulation of the biliary tree where the tassel tip 30 in the deployed configuration of the wire guide 20 minimizes the potential for trauma to the structures of the biliary tree. Finally, the wire guide 20 may be withdrawn such that the tassel tip 30 again takes its delivery configuration within the access device 40.

As indicated in the Background section, newer access devices provide rapid exchange of multiple devices through the provision of exchange ports formed in a distal portion of the access device. For example, this exchange port (or side hole) is placed at about 6 cm from the tip of the catheter or other access device such that only about 6 cm of the wire guide needs to be placed through the internal passageway of the device. Thus, the umbrella shape of the tassel tip 30, which impinges upon the distal end of the access device when it is withdrawn into its internal passageway, serves as an additional identifier to the physician of the wire guides' location. As such, inadvertent disconnection of the wire guide and access device by withdrawing the wire guide through the exchange port is further minimized. Preferably, each of the strands 32 of the tassel tip 30 extend an axial distance much less than 6 cm so that the tassel tip 30 may be located entirely within working channel of these new access devices.

Accordingly, it will be recognized by those skilled in the art that the present invention provides a wire guide and method for cannulation using the wire guide which assists in procedures such as ERCP. The wire guide and method minimize the potential for trauma to the ducts in a biliary tree, especially during deep cannulation. At the same time, the wire guide and method reduce the chances of disconnection of the wire guide from newer access devices which while still providing rapid exchange of such devices.

The foregoing description of various embodiments of the invention has been presented for purposes of illustration and description. It is not intended to be exhaustive or to limit the invention to the precise embodiments disclosed. Numerous modifications or variations are possible in light of the above teachings. The embodiments discussed were chosen and described to provide the best illustration of the principles of the invention and its practical application to thereby enable one of ordinary skill in the art to utilize the invention in various embodiments and with various modifications as are suited to the particular use contemplated. All such modifications and variations are within the scope of the invention as determined by the appended claims when interpreted in accordance with the breadth to which they are fairly, legally, and equitably entitled.

The invention claimed is:

1. A wire guide for intracorporeal procedures, the wire guide comprising:
    a main body having a distal end, the main body defining a longitudinal axis, the distal end of the main body constructed of a plurality of wires stranded together to form the main body, wherein distal portions of the plurality of wires form the plurality of strands of a tassel tip; and the tassel tip formed at the distal end of the main body, the tassel tip defined by a plurality of strands each having a connecting portion, middle portion and a free end portions, the connecting portion connected to the main body at a connection point, the middle portion located between the connecting and free end portion,
    the tassel tip operable between a delivery configuration and a deployed configuration, the free end portions of the plurality of strands positioned adjacent the longitudinal axis in the delivery configuration, the free end portions of the plurality of strands spaced radially from the longitudinal axis in the deployed configuration, the plurality of strands moving away from the longitudinal axis and the middle portions being curved to define atraumatic peaks in the deployed configuration, the free end portions being positioned distally relative to the middle portions in the delivery configuration, the free end portions being positioned proximal to the connection point and pointing proximally in the deployed configuration.

2. The wire guide of claim 1, wherein the free end portions of the plurality of strands are radially spaced apart a distance greater than a diameter of the main body in the deployed configuration.

3. The wire guide of claim 1, wherein the free end portions of the plurality of strands extend proximally alongside the outside of the main body in the deployed configuration.

4. The wire guide of claim 1, wherein each of the plurality of strands has a diameter about equal to or smaller than a radius of the main body.

5. The wire guide of claim 1, wherein the plurality of strands are formed of flexible material having sufficient strength to from an umbrella shape in the deployed configuration.

6. The wire guide of claim 1, further comprising a hub at the distal end of the main body, the hub fixedly banding together the plurality of wires.

7. The wire guide of claim 1, wherein the plurality of strands includes at least four strands.

8. The wire guide of claim 1, wherein the plurality of strands each have a circular cross-sectional shape.

9. The wire guide of claim 1, wherein the plurality of strands each have a non-circular cross-sectional shape.

10. The wire guide of claim 1, wherein the plurality of strands retroflex in the deployed configuration to define an umbrella shape.

11. The wire guide of claim 1, wherein the free end portions are generally straight in the deployed configuration.

12. The wire guide of claim 1, wherein the plurality of strands have sufficient flexibility such that of proximal movement of the main body while the tassel tip is in the deployed configuration intracorporeally, causes the strands to unroll and move back to the delivery configuration.

13. A wire guide for intracorporeal procedures, the wire guide comprising:
  a main body having a distal end, constructed of a unitary solid wire, the main body defining a longitudinal axis; and
  a tassel tip formed at the distal end of the main body, the tassel tip defined by a plurality of strands each having a connecting portion, middle portion and a free end portions, the connecting portion connected to the main body, the middle portion located between the connecting and free end portion, a distal portion of the solid wire connected to the plurality of strands, wherein the distal portion of the solid wire includes a plurality of channels fixedly receiving a portion of the plurality of strands,
  the tassel tip operable between a delivery configuration and a deployed configuration, the free end portions of the plurality of strands positioned adjacent the longitudinal axis in the delivery configuration, the free end portions of the plurality of strands spaced radially from the longitudinal axis in the deployed configuration, the plurality of strands moving away from the longitudinal axis and the middle portions being curved to define atraumatic peaks in the deployed configuration, the free end portions being positioned distally relative to the middle portions in the delivery configuration, the free end portions being positioned proximal to the middle portions in the deployed configuration.

14. The wire guide of claim 13, wherein the plurality of strands are unitarily and integrally formed with the main body, the solid wire of the distal end having longitudinal cuts to define the plurality of strands.

15. The wire guide of claim 14, wherein the strands include outer surfaces having material deformations to improve their flexibility, and smooth inner surfaces.

16. The wire guide of claim 14, wherein each strand has a pre-shaped cross-section, and wherein an inner edge of each strand is curved and includes a filet.

* * * * *

UNITED STATES PATENT AND TRADEMARK OFFICE
CERTIFICATE OF CORRECTION

PATENT NO.          : 8,702,720 B2                         Page 1 of 1
APPLICATION NO.     : 11/743745
DATED               : April 22, 2014
INVENTOR(S)         : Douglas E. McLaren It is certified that error appears in the above-identified patent and that said Letters Patent is hereby corrected as shown below:

In the Claims

Claim 1, Col. 6, Line 47 after the word "end" delete "portions" and insert --portion--.

Signed and Sealed this
Twenty-ninth Day of July, 2014

Michelle K. Lee
*Deputy Director of the United States Patent and Trademark Office*